United States Patent [19]
Huang

[11] Patent Number: 5,984,681
[45] Date of Patent: Nov. 16, 1999

[54] DENTAL IMPLANT AND METHOD OF IMPLANTING

[76] Inventor: Barney K. Huang, 3332 Manor Ridge Dr., Raleigh, N.C. 27603

[21] Appl. No.: 08/922,050

[22] Filed: Sep. 2, 1997

[51] Int. Cl.⁶ .................................................. A61C 8/00
[52] U.S. Cl. ............................................ 433/174; 433/173
[58] Field of Search .................................... 433/172, 173, 433/174, 175, 176

[56] References Cited

U.S. PATENT DOCUMENTS

| | | | |
|---|---|---|---|
| 3,386,169 | 6/1968 | Scialom | 433/173 |
| 3,474,537 | 10/1969 | Christensen | 433/174 |
| 3,579,831 | 5/1971 | Stevens | 433/174 |
| 3,624,904 | 12/1971 | Linkow | 433/173 |
| 3,808,606 | 5/1974 | Tronzo | 433/173 X |
| 3,955,280 | 5/1976 | Sneer | 433/174 X |
| 4,283,176 | 8/1981 | Vajda | 433/173 |

*Primary Examiner*—Nicholas D. Lucchesi
*Attorney, Agent, or Firm*—Coats & Bennett, P.L.L.C.

[57] ABSTRACT

The present invention entails an implant for insertion into the alveolar bone of a patient and wherein the implant is provided with a generally vertically projecting anchoring pin that extends from the implant into the alveolar bone of the patient and effectively interconnects the implant with the alveolar bone. Moreover, the present invention entails a method or process of implanting a dental implant including directly implanting an implant into the extraction cavity after a tooth has been extracted therefrom. As a part of this process, prior to actually implanting, the extraction cavity is reamed so as to be compatible with an optimum size and shaped implant selected from a group of standard implants.

13 Claims, 5 Drawing Sheets

DENTAL IMPLANT AND METHOD OF IMPLANTING

FIELD OF THE INVENTION

The present invention relates to dental implants and methods for implanting such implants, and more particularly to an efficient and effective method of implanting a dental implant where the implant is set immediately after the extraction of a tooth.

BACKGROUND OF THE INVENTION

The natural teeth are often lost as a result of dental disease, trauma or injury. In recent years, more and more dentists and oral surgeons have turned to dental implants as an acceptable and appropriate means to restore a tooth that has been lost because of disease or trauma. Such dental implants offer an attractive alternative to other options because with a dental implant the patient realizes a restoration that closely approximates a natural tooth without having to alter the structure or appearance of adjacent natural teeth which occurs, for example, when a patient chooses a bridge option.

Typically in conventional processes, an implant operation begins with the extraction of the tooth. After extraction, the patient is sent home for a period of time, approximately 3 to 12 months, during which time the extraction or root cavity formed by the extraction is allowed to close and heal. This is because, typically, commercial implants are of a cylindrical shape and consequently do not naturally fit the general taper or conical shape of the extraction cavity. Consequently, conventional cylindrical shaped implants cannot be inserted directly into the natural tapered extraction cavity. Therefore, after extraction, the extraction cavity must be allowed to close through healing. After the root cavity has closed and healed, the patient returns for further procedures. Here, the healed site is drilled to form an implant cavity in the area formally occupied by the extracted tooth. The size of the bore or cavity formed by the drill is slightly less than the diameter of the particular implant selected. Once the implant cavity has been formed, the implant is either inserted into the cavity with friction grip or screwed into the cavity with self-tapping threads. Thereafter, a second healing period follows. Time is required for the bone tissue surrounding the implant to grow up against and mechanically lock the implant in place. Typically, depending on the age of the patient and the site in the mouth, the second healing period can extend for approximately 3 to 12 months. Once integration has been reached, that is where the bony tissue fully grows in direct apposition to the implant, the dentist can install a false teeth or prosthesis onto the implant.

While dental implants are generally desirable, it is obvious that they come with some problems and much inconvenience. It is not uncommon for the period between tooth extraction and the final fitting of the prosthesis to be 6 to 18 months. Moreover, during that extended period, the patient may have to tolerate inconvenience, discomfort and sometimes pain.

Besides the time and inconvenience associated with conventional procedures for implanting, it is also difficult in some cases to properly orient the implant and maintain it stable after the prosthesis has been fitted. Obviously, insertion-type implants may tend to lack substantial implant-bony tissue contact from the outset. This can contribute to longer healing periods. Because of the lack of substantial close bone contact, it can take prolonged periods of time before the implant and the bony tissue integrate. Screw-type implants also are difficult to orient and stabilize. Typically, the thread pattern of screw-type implants require multi turns to set the implant. The hardness of the bony tissue in and around the implant cavity varies. With a multi turn implant, the threads tend to draw the implant towards and through softer bony tissue. This can results in the entire implant misaligning within the alveolar bone structure of the patient.

Finally, implants are typically designed such that they conform to a generally cylindrical configuration. In addition, typical implants are of a single piece construction and do not include additional or auxiliary means for interlocking the implant to the alveolar bone structure. Once the prosthesis has been attached to the top portion of the implant and the patient starts to use the implant to chew food, the stress, vertical and lateral forces, and rotational torques placed on the prosthesis are transferred downwardly to the implant. In cases where the implant is not stable and tightly secured within the implant cavity, the implant tends to rotate and turn under these stresses, forces and torque. This results in the implant becoming loose within the implant cavity and that often results in the implant becoming dislodged from the cavity or being so loose and unstable within the cavity that the same has to be removed from the patient's alveolar bone.

Finally, as noted above, most typical implants that are commercially available today include a cylindrical configuration. Thus, the outer walls are not generally tapered or conical. This cylindrical configuration results in substantial stresses and forces being concentrated at the lower end of the implant and those concentrated stresses and forces tend to loosen the implant and make the implant unstable within the patient's mouth.

SUMMARY AND OBJECTS OF THE INVENTION

The present invention entails a dental implant and a method of implanting that implant which is designed to overcome the drawbacks and problems associated with conventional dental implants and procedures in implanting operations.

First, the method entails setting the implant directly after tooth extraction without interposing a healing period between extraction and implant setting. In carrying out this method, the dentist or oral surgeon selects a reamer that is sized according to the size of an optimum implant. Immediately following extraction, the selected reamer is inserted into the extraction cavity and through a reaming procedure the shape and contour of the extraction cavity is formed to accept the selected implant. After reaming and forming a clean and open cavity, the selected implant is firmly set into the reamed extraction cavity. Thereafter, a healing period follows wherein osseointegration takes place. That is, during this period the bone surrounding the implant is allowed to grow and heal up against the implant so as to securely set the implant within the reamed extraction cavity. After integration has been achieved, the dentist can then secure a false tooth or prosthesis to the top of the implant.

The dental implant of the present invention is provided with a generally vertically projecting anchor pin for interconnecting the implant with the alveolar bone of the patient. In one embodiment, the implant includes upper and lower portions with the upper portion having an offset portion that projects outwardly with respect to the lower portion. The anchoring pin and implant are designed such that the anchoring pin projects downwardly from the offset portion into the alveolar bone of the patient. In a second design, the dental implant of the present invention includes an access opening formed in the top of the dental implant and a throughbore that extends from the access opening through the wall structure of the dental implant. To secure and anchor this design within the alveolar bone of the patient, the anchoring pin is inserted through the access opening into the throughbore where the anchoring pin is screwed or set within an adjacent portion of the patient's alveolar bone. In both cases, the anchoring pin that interconnects the implant with the alveolar bone tends to securely stabilize the implant within the alveolar bone and generally prevents the implant from rotating under stress or load.

It is therefore an object of the present invention to provide a method of performing a dental implant that reduces the time period that customarily takes place between tooth extraction and the placement of a false tooth or prosthesis on the implant.

A further object of the present invention is to provide a method for performing a dental implant operation that allows the implant to be inserted or set within the tooth cavity immediately after extraction.

Also an object of the present invention resides in the provision of a dental implant process that reduces surgical time and the cost of an implant operation.

Another object of the present invention is to provide a method for surgically implanting an implant that does not depend upon the extraction cavity healing and closing and which does not involve drilling an implant cavity into the alveolar bone of the patient.

Still a further object of the present invention is to provide a method of performing a dental implant that employs a reaming process after extraction that sizes the extraction cavity for receiving an implant that is itself sized according to the size of the root portion of the extracted tooth.

Another object of the present invention is to provide a dental implant that can be easily anchored into the alveolar bone of a patient.

Still a further object of the present invention is to provide a dental implant that includes quick-turn threads that enables the implant to be screwed in place within the extraction cavity formed within the alveolar bone with a turn of 360° or less.

Another object of the present invention resides in the provision of a dental implant that includes an anchoring pin that extends generally downwardly from the top portion of the implant and connects with the alveolar bone and which effectively interconnects the implant with the alveolar bone.

Other objects and advantages of the present invention will become apparent and obvious from a study of the following description and the accompanying drawings which are merely illustrative of such invention.

DETAILED DESCRIPTION OF THE INVENTION

Figure 1:
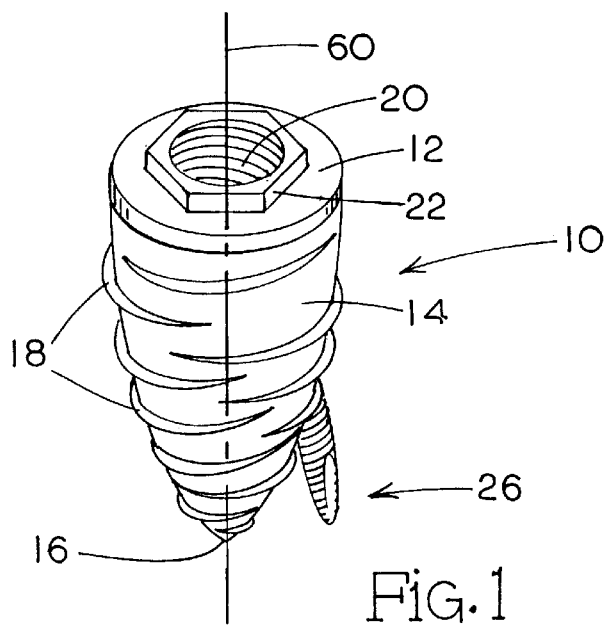
FIG. 1 is a perspective view of the dental implant of the present invention.
Figure 2:
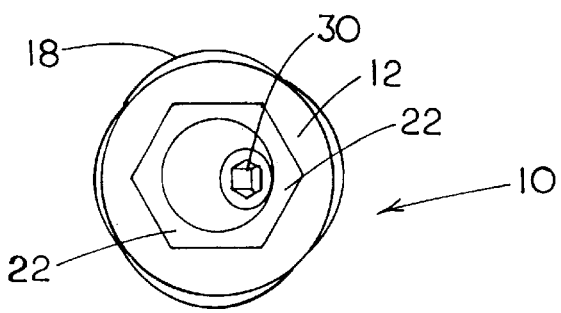
FIG. 2 is a top plan view of the dental implant shown in FIG. 1.
Figure 3:
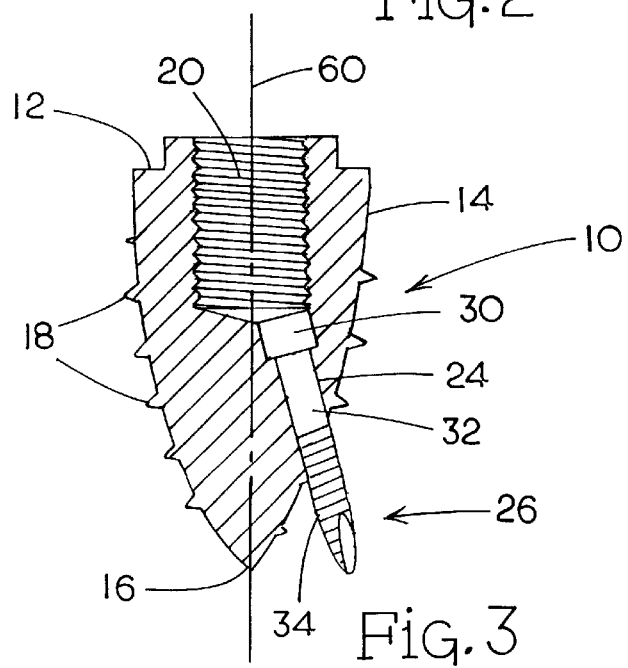
FIG. 3 is a cross-sectional view of the dental implant shown in FIGS. 1 and 2.

With further reference to the drawings, and particularly FIGS. 1–3, the dental implant of the present invention is shown therein and indicated generally by the numeral 10. Dental implant 10 includes an upper and lower portion with at least the lower portion assuming a generally tapered and conical shape. While various materials can be used to construct the implant 10 of the present invention, it is widely recognized that one of the more suitable materials for dental implants is titanium. This is due, in part at least, to the fact that titanium is a very strong and light metal and is highly resistant to corrosion and degradation even though when implanted the implant assumes a position embedded within the alveolar bone structure of a patient.

Turning to dental implant 10, it is seen that the same includes a top surface 12, a surrounding wall structure 14, and a lower terminal end 16. As seen in FIG. 1, a major portion of the side wall structure 14 is tapered. However, about the top of the implant 10 there is a thin ring area that is generally flat and untapered. Formed around at least a portion of the surrounding wall structure 14 is an array of quick-set thread segments 18. Unlike conventional implant threads, the threads 18 are not continuous. As seen in the drawings, the individual thread segments 18 have a beginning portion and an ending portion. In a preferred embodiment, the thread segments 18 can extend as little as one-fourth to one-half turn or may encompass multiple turns around the implant. This means that the entire implant 10 can be set and secured within a cavity formed within the patient's alveolar bone by simply turning the implant a number of turns or even one turn or less. Preferably, the quick-set threads 18 are designed such that the implant can be turned and securely set by two to three turns or less of the implant. As will be appreciated from subsequent portions of this disclosure, the threads 18 are turned into the surrounding alveolar bone structure of the patient and in the process securely set and station the implant 10 in an upright position within an extraction cavity within the alveolar bone of the patient.

In this disclosure, alveolar bone is used to identify that bone structure in a patient's mouth in which the patient's teeth are found. Thus, the term "alveolar bone" refers to both the upper and lower bone structure that anchors and supports the patient's teeth.

Formed in the top portion of the implant 10 is a threaded bore or access opening 20. As seen in the drawings, particularly FIG. 3, the opening 20 extends down from the top surface 12 to an intermediate depth within the implant 10. As noted above, opening 20 is threaded. This enables the false tooth, the prosthesis or intermediate abutment to be threaded into the implant 10. Typically, the prosthesis or false tooth (not shown) includes an anchoring stud or screw extending from the bottom thereof with the anchoring stud or screw being threaded to fit within the threaded opening 20.

Consequently, the false tooth, prosthesis or intermediate abutment is simply threaded into the opening 20 so as to secure the prosthesis, false tooth or intermediate abutment to the top surface 12 of the implant. A detailed discussion of the prosthesis, false tooth or intermediate abutment and its connecting structure is not dealt with herein in detail because such is not per se material to the present invention and further because techniques and procedures for securing a prosthesis or false tooth to a threaded opening of an implant is well-known and appreciated in the art.

Moreover, the opening 20 functions as an access opening. As will be understood from subsequent portions of this disclosure, an anchoring pin will extend through a throughbore formed in the implant. Access opening 20 allows the dentist or oral surgeon to gain access to the anchoring pin and to turn the anchoring pin with a tool that will extend through the access opening 20.

Formed on the top surface 12 around the upper edge of the opening 20 is a turning nut 22. Turning nut 22 is preferably integral with the implant 10 and is used to turn and rotate the implant 10 during the course of securing and stationing the implant within a formed cavity within the patient's alveolar bone. More particularly, the dentist or oral surgeon engages the turning nut 22 with a rotating tool and after the implant 10 has been set within the formed receiving cavity, the turning or rotating tool is turned causing the turning nut 22 to be turned resulting in the entire implant being rotated and set within the formed receiving cavity.

As particularly shown in FIG. 3, there is provided a throughbore 24 that extends from the bottom of the access opening 20 to and through a side of the implant 10. In FIG. 3, it can be seen where the throughbore 24 is disposed at a slight angle with respect to the major or longitudinal axis 60 of the implant. Further, it is seen where the upper portion of the throughbore 24 includes a seat designed to accept the head of an anchoring pin or screw to be hereafter described.

The implant 10 of the present invention is provided with an anchoring pin or screw, indicated generally by the numeral 26, that functions to securely anchor the implant within the alveolar bone of the patient. The anchoring pin 26 prevents the implant 10 from rotating or becoming loose when the implant is embedded within the alveolar bone of the patient. Anchoring pin 26 is of the self-tapping type and includes a screw head 30, a smooth shank portion 32, and a threaded self-tapping portion 34. As will be apparent from this specification, in the case of the implant design shown in FIGS. 1–3, the anchoring pin 26 is inserted downwardly through the access opening 20 and into the throughbore 24. Once in the throughbore 24, the screw head 30 is engaged with a turning tool such as a screw driver or Allen wrench that extends through the access opening 20, and the anchoring pin 26 is turned causing the self-tapping threads 34 to be pulled within bone structure adjacent to the implant 10. The anchoring pin 26 further anchors and secures the implant in place and is particularly designed to prevent the implant 10 from rotating or becoming loose under stress or load.

Figure 7:
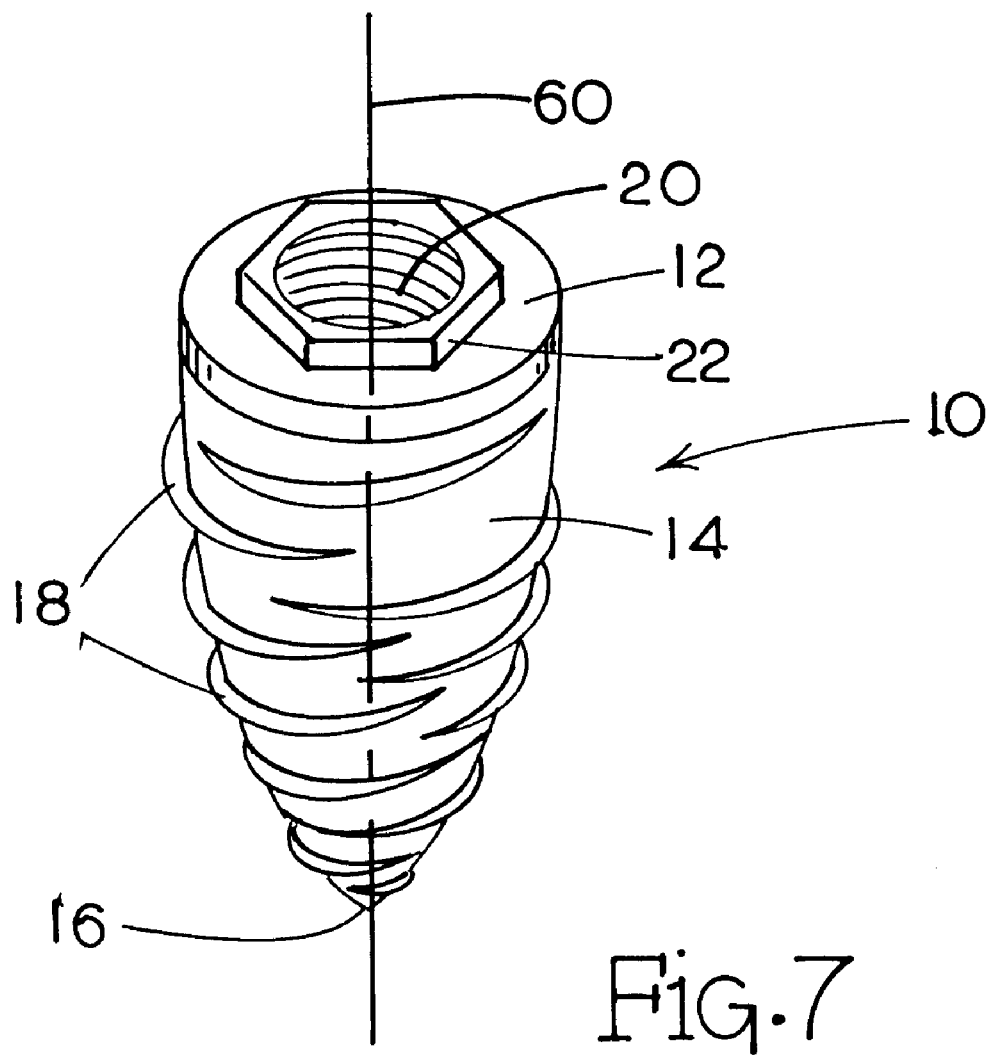
FIG. 7 is a perspective view of the dental implant of the present invention shown without an anchoring pin.

At this point, it should be stated that the implant 10 of the present invention can be utilized without an anchoring pin 26. For example, as illustrated in FIG. 7, the implant 10 can be inserted and stationed within the alveolar bone of a patient by simply screwing the implant into the alveolar bone. In certain cases, the utilization of an anchoring pin may assist in stabilizing and preventing the implant from rotating under load or stress. However, the implant 10, as simply disclosed in FIG. 7, can be utilized. A detailed discussion of the implant shown in FIG. 7 will not be dealt with herein because it is substantially similar to the design shown in FIGS. 1–3 except that there is no anchoring pin or throughbore for receiving the anchoring pin provided.

Figure 4:
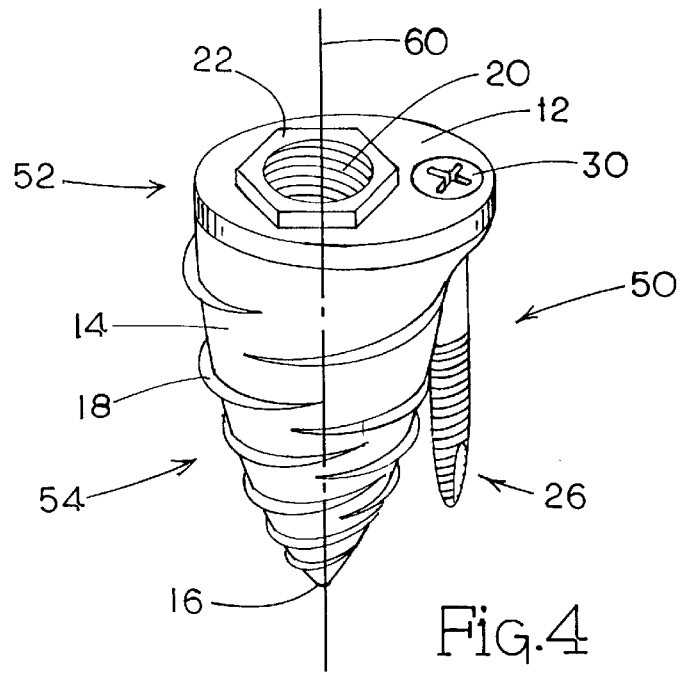
FIG. 4 is a perspective view of a second design for the dental implant of the present invention.
Figure 5:
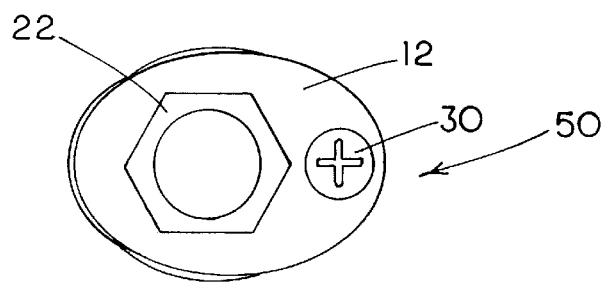
FIG. 5 is a top plan view of the dental implant shown in FIG. 4.
Figure 6:
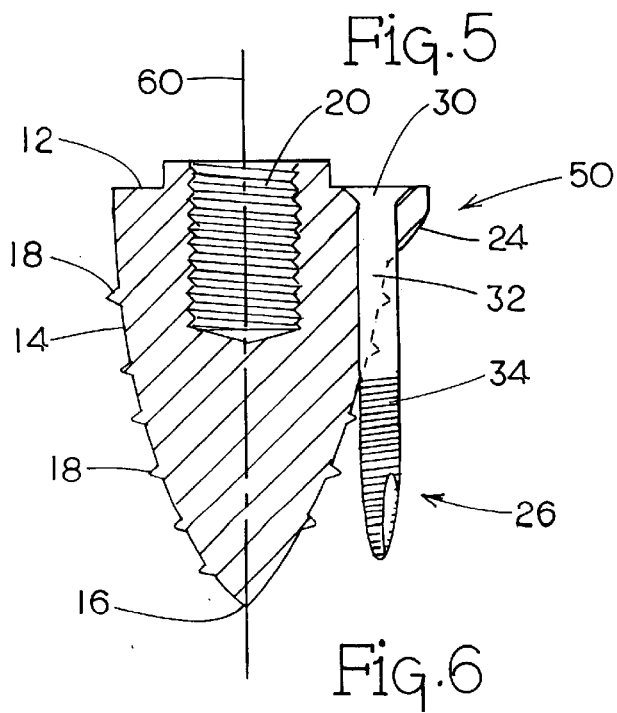
FIG. 6 is a cross-sectional view of the dental implant design shown in FIGS. 4 and 5.

Now, turning to FIGS. 4–6, a second design for the implant of the present invention is shown therein and indicated generally by the numeral 50. The second implant design includes an upper portion indicated generally by the numeral 52 and a lower portion indicated by the numeral 54. The upper portion 52 includes an offset portion that extends generally outwardly with respect to the lower portion 54. Preferably the lower portion 54 of the implant 50 is of a generally conical or tapered shape while the top portion of the implant assumes a generally elliptical configuration.

Implant 50 of the second design includes a top surface 12, a surrounding wall structure 14 and a lower terminal tip 16. Like the first design shown in FIGS. 1–3, the implant 50 includes a series of quick-turn threads 18 formed about the wall structure 14 of the implant. Quick-turn threads 18 are designed to secured the implant within the alveolar bone of a patient with approximately two to three turns or less.

Formed on the top surface 12 is a turning nut 22 that is generally concentric with the lower portion 54 of the implant 50. Concentric with the turning nut 66 and the lower portion 54 of the implant is a threaded bore 20. The threaded bore 64 enables a prosthesis or false tooth to be secured to the implant 50 by way of a coupling stud.

Formed in the offset portion of the upper portion 52 of the implant 50 is a generally vertical throughbore 24. Throughbore 24 includes a counter-sunken upper seat for receiving the head of an anchoring pin indicated generally by the numeral 26. Anchoring pin 26 in this embodiment includes a screw head 30, a smooth shank portion 32, and a self-tapping threaded portion 34. Although the orientation of the throughbore 24 can be varied, in the design shown in FIGS. 4–6, the throughbore is generally parallel with the major or longitudinal axis 60 of the threaded bore 20. As in the case of the first design shown in FIGS. 1–3, the anchoring pin 26 is screwed into the patient's alveolar bone structure surrounding the implant and serves to securely anchor the implant 50 and generally prevents the implant from rotating or loosening while a load or stress is being placed on the implant by the patient eating or chewing.

The implants 10 and 50 of the present invention are designed to be set within the patient's alveolar bone immediately after a tooth has been extracted. It should be pointed out, however, that the implants 10 and 50 disclosed herein can be implanted within a patient's alveolar bone at any time after extraction including cases where the extraction cavity has completely healed and closed.

Turning to the method of implanting, after extraction a selected size reamer is used to ream and clean the extraction cavity. It is contemplated that a series of different size standard implants would be available. Such a kit of standard implants may vary in length, shape and maximum diameter. For example, the maximum diameter of that portion of the implant that is actually screwed into the alveolar bone may range from approximately 3.5 millimeters to 6.0 millimeters. Typically, it is contemplated that the kit of standard implants would include a comparable range of diameters in increments of approximately 0.10 millimeters to 0.50 millimeters. Accordingly, after extraction, a particular size implant would be selected from a group of standard implant sizes. The selection of the implant would be based on a review of the shape and size, diameter and length, of the root portion of the extracted tooth. For example, this can be accomplished by various approaches. This can be accomplished through a visual inspection of the root portion of the extracted tooth and by using a measurement instrument such as a micrometer to determine the precise diameter or cross-sectional area of the root portion of the extracted tooth. In addition, it is contemplated that the selection of the appropriate size implant can be carried out by a computer process wherein the computer would measure critical dimensions of the root portion of the extracted tooth and then through the utilization of specific software the optimum implant from the standard group could be selected. Based on these criteria, an implant would be selected that would tend to approximate the size and shape of the root structure of the tooth extracted. Once the appropriate implant has been selected from the group of standard implants, then the dentist or oral surgeon selects a corresponding or matching reamer from a reamer set.

In one embodiment of the present invention, for each implant of the standard group, there would be provided a standard reamer for shaping the extraction cavity to ideally conform to the selected implant. All of the reamers forming the reaming kit would preferably include a lower conically shaped bottom. As a practical matter, the effective cross-sectional area or diameter of the reamer would be slightly smaller than the diameter of selected implant including the threaded segments 18. This is because it is important to ream the extraction cavity to form a reamed cavity that will enable the selected implant to be placed in the reamed cavity and turned such that the quick-turn threads 18 are turned into the adjacent surrounding structure of the alveolar bone.

It is contemplated that the dental implant design shown in FIGS. 4–6 would be suitable for replacing molars while the design shown in FIGS. 1–3 would be more appropriate for the front teeth and non-molars. However, it should be appreciated that there may be certain situations where either implant design would be appropriate.

In any event, after a patient's tooth has been extracted and the extraction cavity has been properly reamed, cleaned and treated, the lower portion of a selected implant is placed within the reamed cavity. After the implant has been aligned with the reamed cavity, the dentist or oral surgeon then engages the turning nut 22 of the implant 10, 50 and rotates the turning nut 22 causing the implement to be set in the cavity.

After the implant has been turned and set, the next step in the process is to effectively connect the implant with an adjacent portion of the bone structure through the anchoring pin 26. In the case of the first design shown in FIGS. 1–3, the anchoring pin 26 is passed through the access opening 20 and inserted into the throughbore 24. Thereafter, the dentist or oral surgeon gains access to the screw head 30 through the access opening 20. By extending a screw downwardly through the access opening 20 and engaging the screw head 30, the anchoring pin 26 can be screwed into the adjoining alveolar bone structure.

In the case of the second design shown in FIGS. 4–6, the implant 50 is set within the reamed cavity in the same manner. However, it is preferable that the throughbore 24 and the axis 60 be aligned with the general contour and shape of the alveolar bone. This means that in the case of a molar extraction that the lower portion 54 and the throughbore 24 are oriented generally in a fore and aft configuration and not a transverse configuration. See FIG. 8. However, in certain cases it may be plausible to orient the throughbore 24 and the axis of the lower portion 54 such that they do extend transversely across the alveolar bone. In any event, after the implant has been turned and securely set within the alveolar bone, then the next step is to secure the anchoring pin or screw 26. Anchoring pin or screw 26 is inserted through the throughbore 24 and then screwed downwardly into the underlying alveolar bone structure that lies adjacent the lower portion 54 of the implant 50. Typically, the anchoring pin 26 is screwed downwardly until the screw head 30 sets in the seat formed about the upper portion of the throughbore 24.

To prevent microleakage through the throughbore 24, the throughbore and anchoring pin are sized such that there is relatively close contact between the anchoring pin 26 and the throughbore 24. This effectively seals the throughbore. Additional steps can also be implemented to assure that there is no microleakage through the throughbore. For example, the throughbore 24 along with screw head 30 and the smooth shank portion 32 of the anchoring pin 26 can all be Teflon coated to provide a very tight and leakproof seal down through the throughbore 24. In addition, conventional dental sealant materials can be used to coat the throughbores and the anchoring pins such that once the anchoring pins are set in place, the sealant material forms an impervious seal between the throughbore and the anchoring pin. Further, once the anchoring pin 26 has been set the entire top of the implant can be coated and sealed with a conventional dental sealant material. This, after curing, would form a complete seal across the entire top of the implant. These processes for sealing the throughbore 24 can be applied to either the design of FIGS. 1–3 or the design shown in FIGS. 4–6.

In forming the reamed cavity and selecting the appropriate size implant, care is taken to assure that the top of the implant when set and anchored within the alveolar bone, will lie just below the upper gum level. See FIGS. 8 and 9. After the implant has been set, the implant site is closed by taking the adjacent soft tissue, referred to as the gingival flap, and securing, by stitching for example, that adjacent soft tissue over the implant. Alternatively, the top of the implant can be closed with a conventional temporary dental cap. After the implant site has been closed, an integration and healing period follows. That is, before the prosthesis or a false tooth is secured to the implant, the alveolar bone and bony structure surrounding the implant is allowed to heal and to grow in direct apposition to the implant. This is commonly called osseointegration. That is, through this healing process the bone structure remodels and heals in intimate contact with the implant, fully integrating the implant with the alveolar bone structure. This healing and integration period can vary. Typically, it is contemplated that this period will last approximately 3 to 12 months, depending on the age of the patient and general health and well-being of the patient's bone and surrounding tissue structure.

After this healing and integration period have been completed, the patient is then ready for the prosthesis or false tooth to be attached. As pointed out above, in conventional fashion, the prosthesis or false tooth includes an anchoring stud that is threaded to fit into the threaded opening 20. In either case, the healed soft tissue is cut open or the temporary cap is removed to gain access to the top of the implant. After cleaning and treating the upper surface of the implant and the surrounding soft tissue, the dentist or oral surgeon then screws the prosthesis or false tooth into the threaded opening 20.

Figure 9:
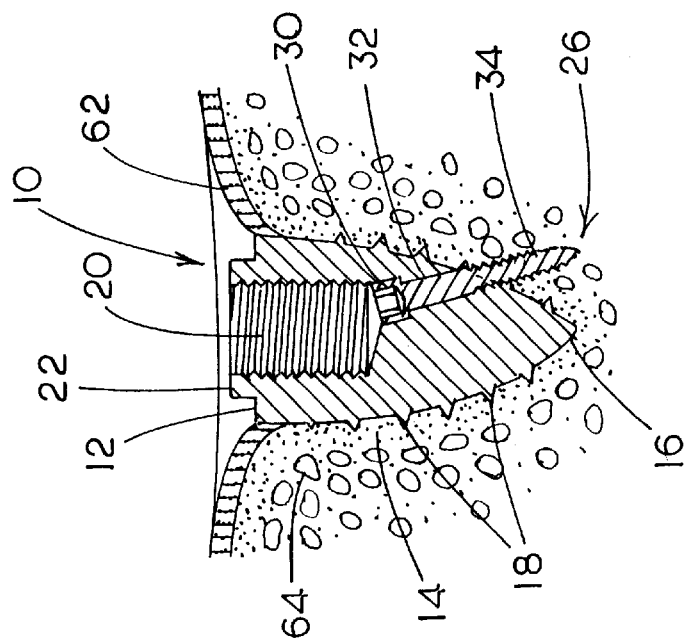
FIG. 9 is a cross-sectional view of the implant of FIGS. 1–3 implanted within the alveolar bone of a patient.
Figure 8:
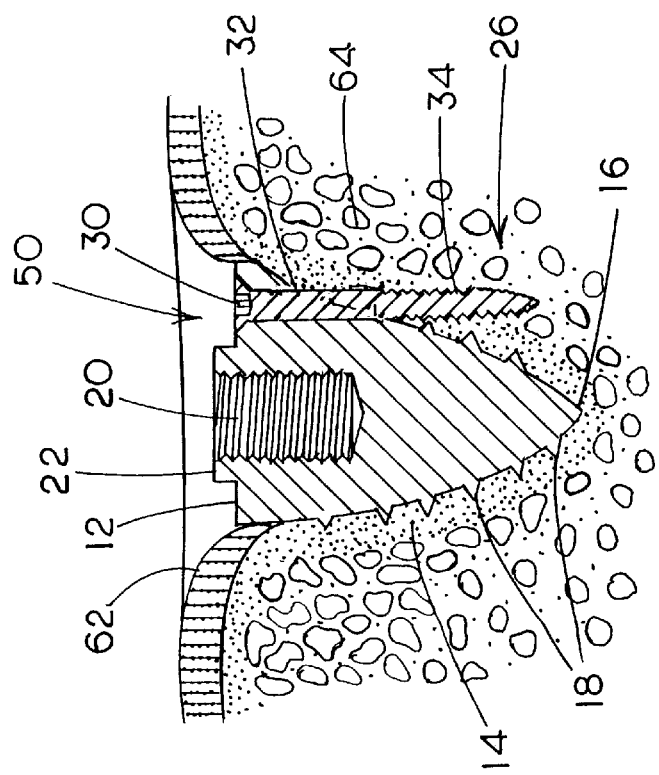
FIG. 8 is a cross-sectional view of the implant of FIGS. 4–6 implanted within the alveolar bone of a patient.

As seen in FIGS. 8 and 9, the implants 10 and 50, once securely anchored within the alveolar bone lie just below the top of the tissue surface that is schematically shown and referred to by numeral 62. Note that in each case, the anchoring pin 26 effectively couples the implants 10 and 50 to the surrounding alveolar bone structure that is referred to by the numeral 64. FIGS. 8 and 9 are longitudinal sectional views through the alveolar bone. Consequently, it is seen that the anchoring pin 26 in the case of both implants is disposed in the longitudinal direction around the alveolar bone 64. This is contrasted to cases where the implant and the anchoring pin 26 could be disposed transversely of the alveolar bone 64. But as shown in FIGS. 8 and 9, the anchoring pin or screw functions to securely stabilize the implant and generally prevents the implant from rotating or becoming loose due to a load including lateral or vertical forces. Also, note in FIGS. 8 and 9 that at least the lower portions of the implants are generally tapered or shaped conically. This reduces stress on the lower terminal ends of the implants. Moreover, because of the tapered nature of the lower portions of the implant, vertical and lateral forces can be more uniformly distributed over the area of the alveolar bone surrounding the implant.

The method or process of implanting the implants 10 and 50 of the present invention has been discussed in some detail above. However, it may be beneficial to review the flowchart of FIG. 10 which shows the basic steps involved in placing the implant of the present invention into the alveolar bone of a patient. First, it will be appreciated that the process or method of the present invention entails either placing the implant directly after tooth extraction or in the alternative the process entails implanting after the extraction cavity has had time to heal and close.

Figure 10:
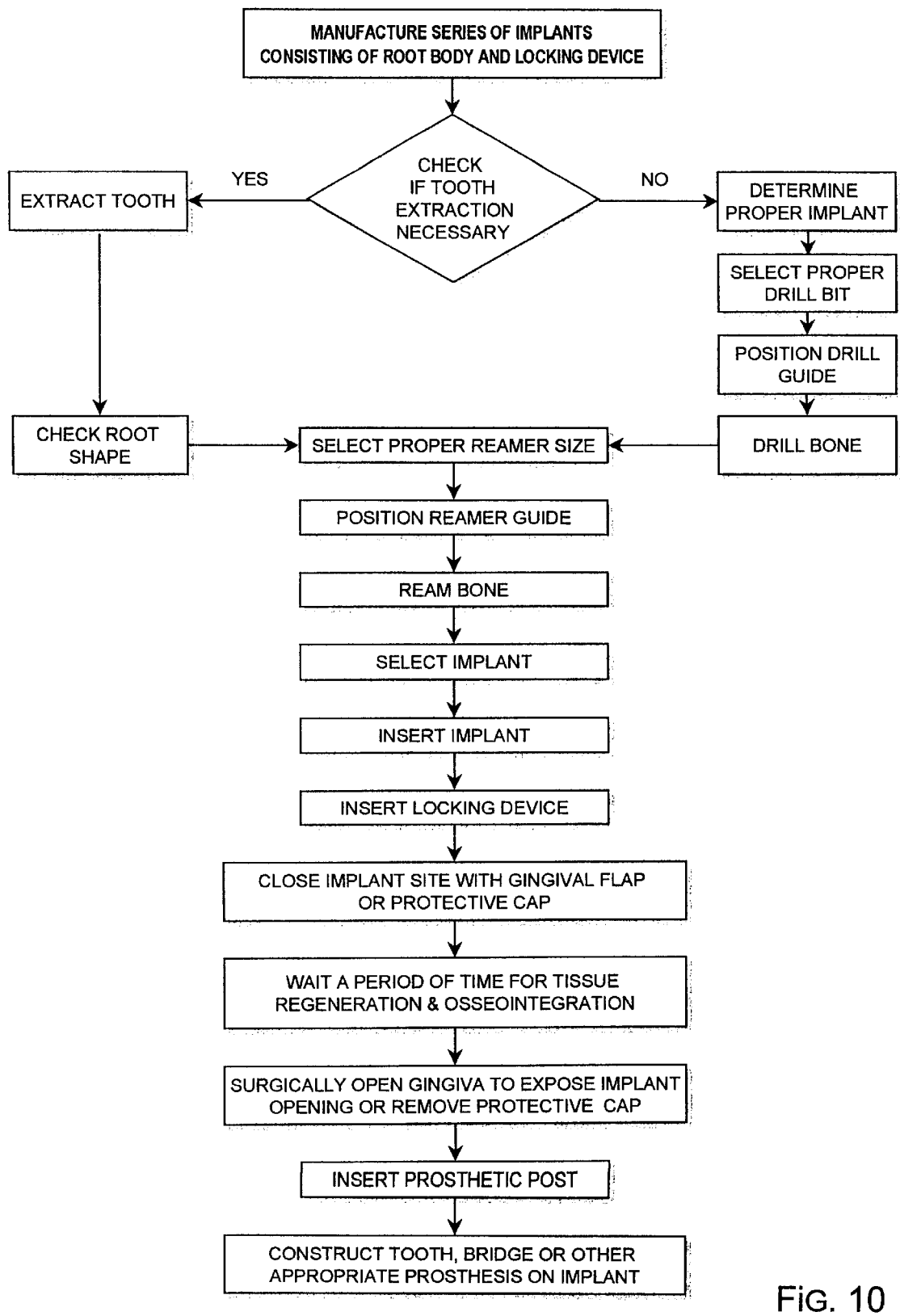
FIG. 10 is a flowchart illustrating the basic process of implanting the implant of the present invention directly after tooth extraction or after the extraction cavity has closed and healed.

A top right-hand portion of the flowchart of FIG. 10 depicts the steps involved when the dentist or oral surgeon is faced with implanting after the extraction cavity has healed and closed. Note that the first step herein is to determine the proper size implant from a standard kit or standard group of implants. Since the extraction cavity has now become closed and healed, the particular implant is selected based on the size and condition of the implant site. In any event, after the proper implant has been selected, the next step entails drilling a receiving cavity through the gum and alveolar bone of the patient at the implant site. The particular drill is selected based on the optimum size implant selected from the standard group of implants. But in any event, a drill guide is utilized and the selected drill bit is directed downwardly through the drill gauge into the alveolar bone of the patient creating an implant cavity. Once the bore has been created then the next step is to utilize a selected reamer, again based on the implant selection. This also occurs after a tooth has been extracted and it is the intent of the dentist or oral surgeon to immediately set the implant. In either case, a select reamer is chosen based on the optimum size of the implant to be used. A reamer guide can be secured about the extraction cavity or the cavity formed by the drill. The reamer is preferably of a conical or tapered shape and would generally conform to the shape of the original root structure of the extracted tooth. The cavity is reamed and the extraneous material resulting from the reaming is removed. Thereafter, as discussed herein before, the implant is inserted within the reamed cavity and anchored within the alveolar bone. Next, the anchoring pin or screw 26 is extended through the throughbore 24 and screwed into the alveolar bone adjacent the implant. This again couples the implant to the alveolar bone and prevents rotation and loosening.

After the implant has been set, then the implant site is closed in order that the same can heal for a period of time. A temporary cap can be used but in most cases it would be preferred that the gingival flap be returned across the top of the implant so as to close the same. Thereafter, a process of osseointegration occurs. This is where the bone structure remodels and heals in intimate contact with the implant. The time for healing can vary from approximately 3 to 12 months depending on the age of the patient and other factors. It is postulated, however, that in the case where implanting takes place immediately after extraction that there is an improved chance for quicker healing and osseointegration because the alveolar bone has not been subjected to the trauma of drilling that takes place in cases where the implanted site has healed and closed.

After a sufficient time has passed for osseointegration to occur, the dentist or oral surgeon then returns to the implant site and surgically opens the gingival flap and creates a clean base for the prosthesis. Next, the prosthesis or false tooth is constructed and attached.

One principal advantage of the dental implant of the present invention is that the anchoring pin securely stabilizes the implant within the alveolar bone structure of the patient. The presence of the anchoring pin 26 interlocking the implants 10 and 50 with the alveolar bone 64 generally prevents the implant from rotating or loosening under any load.

Further, the conical or tapered shape of the lower portion of the implant enables the implant as a whole to distribute loads and forces being applied against the implant and does not concentrate these stresses and loads on the lower terminal end of the implant which in conventional applications often results in the implant becoming loose and being required to be extracted. Further, the method of the present invention significantly reduces the total time that generally lapses between tooth extraction and the addition of a prosthesis to the implant. This is because there is no time period required for the extraction cavity to heal and close before the actual implant is implanted. Finally, the overall process reduces the amount of surgery required on the patient's alveolar bone and generally reduces costs.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended Claims are intended to be embraced therein.

What is claimed is:

1. A dental implant comprising: an implant for insertion into the alveolar bone of a patient, a generally vertically projecting anchoring pin for interconnecting the implant with the alveolar bone of the patient; and wherein the implant includes a threaded portion having a set of segmented quick-turn threads designed to anchor the implant within the alveolar bone.

2. The dental implant of claim 1 wherein the implant and anchoring pin each include a longitudinal axis and wherein when implanted within the alveolar bone the axis of the implant and anchoring pin extend in general parallel relationship.

3. The dental implant of claim 1 wherein the implant and the anchoring pin, when implanted, are longitudinally aligned with the alveolar bone of the patient.

4. The dental implant of claim 1 wherein the anchoring pin includes a threaded portion for engaging the alveolar bone.

5. The dental implant of claim 1 wherein the implant includes an anchor pin throughbore formed therein and accessible from the top of the implant, and wherein the anchoring pin extends through the anchor pin throughbore and into the alveolar bone.

6. The dental implant of claim 5 wherein the implant includes an access opening that is opened about the top of the implant and wherein the anchor pin throughbore extends from the access opening through the implant.

7. The dental implant of claim 6 wherein the access opening includes a surrounding wall structure and wherein the anchor pin throughbore extends from the wall structure of the access opening through the body of the implant.

8. A dental implant comprising: an implant for insertion into the alveolar bone of a patient and a generally vertically projecting anchoring pin for interconnecting the implant with the alveolar bone of the patient; and wherein the implant includes upper and lower portions with the upper portion including an offset portion that projects outwardly with respect to the lower portion, and wherein the anchoring pin projects downwardly from the offset portion and into the alveolar bone of the patient.

9. The dental implant of claim 8 wherein the offset portion of the implant includes a bore formed therein and wherein the anchoring pin extends through the bore.

10. A dental implant comprising: an implant for insertion into the alveolar bone of the patient; the implant including an upper opening for receiving a false tooth, prosthesis, or other abutment; an anchoring pin throughbore extending from the upper opening through the implant such that the throughbore is accessible from the upper opening; and an anchoring pin accessible through the upper opening and projecting through the throughbore for extending into the alveolar bone and anchoring the implant.

11. The dental implant of claim 10 wherein the anchoring pin extends generally vertically relative to the implant.

12. The dental implant of claim 10 wherein the implant includes a threaded portion having a set of quick-turn threads designed to anchor the implant within the alveolar bone of the patient with approximately two to three turns of less.

13. The dental implant of claim 10 wherein the implant includes a conical shaped lower end portion.

* * * * *